(12) United States Patent
Tsaur

(10) Patent No.: US 6,906,016 B1
(45) Date of Patent: *Jun. 14, 2005

(54) PERSONAL PRODUCT LIQUID CLEANSERS COMPRISING COMBINED FATTY ACID AND WATER SOLUBLE OR WATER SWELLABLE STARCH STRUCTURING SYSTEM

(75) Inventor: Liang Sheng Tsaur, Norwood, NJ (US)

(73) Assignee: Unilever Home & Personal Care USA, a division of Conopco, Inc., Greenwich, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/849,100

(22) Filed: May 19, 2004

(51) Int. Cl.[7] .................................................. A61K 7/00
(52) U.S. Cl. ....................... 510/130; 510/156; 510/424; 510/462; 510/474; 424/70.1
(58) Field of Search ................. 510/130, 156, 510/424, 462, 474; 424/70.1

(56) References Cited

U.S. PATENT DOCUMENTS

| | | | |
|---|---|---|---|
| 3,580,853 A | 5/1971 | Parran, Jr. | |
| 5,085,857 A | 2/1992 | Reid et al. | |
| 5,132,037 A | 7/1992 | Greene et al. | |
| 5,234,619 A | 8/1993 | Greene et al. | |
| 5,290,470 A | 3/1994 | Dutcher | |
| 5,308,526 A | 5/1994 | Dias et al. | |
| 5,360,580 A | 11/1994 | Dotolo et al. | |
| 5,439,682 A | 8/1995 | Wivell et al. | |
| 5,518,647 A | 5/1996 | Zocchi et al. | |
| 5,661,189 A | 8/1997 | Grieveson et al. | |
| 5,700,455 A | * 12/1997 | Hinterwaldner et al. . | 424/70.14 |
| 5,854,293 A | 12/1998 | Glenn, Jr. | |
| 5,905,062 A | 5/1999 | Elliott et al. | |
| 5,952,286 A | 9/1999 | Puvvada et al. | |
| 6,001,344 A | 12/1999 | Villa et al. | |
| 6,077,816 A | 6/2000 | Puvvada et al. | |
| 6,172,019 B1 | 1/2001 | Dehan et al. | |
| 6,248,338 B1 | * 6/2001 | Muller et al. ................ | 424/401 |

FOREIGN PATENT DOCUMENTS

| | | |
|---|---|---|
| WO | 92/18100 | 10/1992 |
| WO | 94/03152 | 2/1994 |
| WO | 94/17166 | 8/1994 |
| WO | 94/18737 | 8/1994 |
| WO | 97/48378 | 12/1997 |

OTHER PUBLICATIONS

U.S. Appl. No. 10/849,627, filed May 19, 2004, Tsaur et al., Personal Product Liquid Cleansers Stabilized With Starch Structuring System.
U.S. Appl. No. 10/849,408, filed May 19, 2004, Zhang et al., Soap Bars Comprising Synergiestically High Levels of Both Free Fatty Acid and Filler.

* cited by examiner

Primary Examiner—Necholus Ogden
(74) Attorney, Agent, or Firm—Ronald A. Koatz

(57) ABSTRACT

The invention relates to liquid cleansers which comprise water soluble or water swellable starch combining with linear $C_8$ to $C_{13}$ fatty acid to structure the composition.

22 Claims, No Drawings

PERSONAL PRODUCT LIQUID CLEANSERS COMPRISING COMBINED FATTY ACID AND WATER SOLUBLE OR WATER SWELLABLE STARCH STRUCTURING SYSTEM

FIELD OF THE INVENTION

The present invention relates to personal product, liquid cleansing compositions containing novel structuring system for stabilizing (e.g., preventing phase separation) skin benefit agent (e.g., emollient and/or particles) in said compositions. In particular, the compositions provide good consumer desirable properties (e.g., lathering, non-stringy, non-lumpy appearance) while maintaining good stability (e.g. stable both at room temperature and at 45° C. over three weeks without visible phase separation)

BACKGROUND

In addition to cleaning, another highly desirable characteristic of personal cleanser/shower gel type compositions is to deliver consumer perceivable (e.g., sensory or visual) benefits from the compositions to the skin. One important way of achieving this result is through deposition of benefit agent (e.g., emollient oils and/or of surfactant-insoluble inorganic particles). In turn, this may require incorporation of high levels of such oil or inorganic particles into the cleanser/shower gel composition.

Unfortunately, such dual cleansing and moisturizing compositions are difficult to formulate because cleansing ingredients, in general, tend to be incompatible with moisturizing ingredients. For example, emulsified oil droplets, especially hydrocarbon oil droplets, tend to phase separate from liquids during storage and to form a separate layer at the top of the liquid cleanser.

Also, emollient oils often tend to depress foaming/lathering of cleansing ingredients, especially when the level of surfactants in the liquid cleanser is relatively low (e.g., below about 25% by wt.). However, liquid cleansers containing relatively low level of surfactants and having good lather properties are highly desired because the lower surfactant levels tend to make the composition more mild, to lower cost and to facilitate processing.

Accordingly, there is a need in the art for compositions which contain low level of cleansing ingredients, which are both mild and capable of producing abundant lather, and which also can deliver moisturizing or other active ingredients. In addition, such compositions should stay physically stable at both ambient and elevated storage temperature.

Liquid cleansers, which can deliver skin benefit agents to provide some kind of skin benefit, are known in the art. For example, one method of enhancing delivery of benefit agent to the skin or hair is using cationic polymers such as Polymer JR® from Amerchol or Jaguar® from Rhone Poulenc. This method is disclosed, for example, in U.S. Pat. No. 3,580,853 to Parran et al, U.S. Pat. No. 5,085,857 to Reid et al., U.S. Pat. No. 5,439,682 to Wivell et al; or in WO 94/03152 (assigned to Unilever), WO 92/18100 (assigned to Procter & Gamble) or WO 97/48378 (assigned to Procter & Gamble).

Another method of enhancing delivery of benefit agents to the skin or hair is using large droplets of viscous oils as is described in U.S. Pat. No. 5,661,189 to Grieveson (assigned to Unilever) and U.S. Pat. No. 5,854,293 (assigned to Procter & Gamble).

In addition, the art discloses that physical stability of, for example, an emollient oil cleanser system requires the presence of some sort of suspending or stabilizing agent. U.S. Pat. No. 5,308,526 to Dias et al and U.S. Pat. No. 5,439,682 to Wivell et al, for example, teach the use of crystalline ethylene glycol long chain esters (e.g., ethylene glycol distearate) as suspension agents to prevent the separation of oil droplets from the liquid. There is no disclosure of a water soluble or water swellable starch in combination with fatty acid as a structuring system to provide enhanced stability.

U.S. Pat. No. 5,518,647 to Zocchi (assigned to Colgate) teaches an emulsion system combining long chain ethoxylated alcohol, free fatty carboxylic acid and water soluble cationic polymer to achieve physical stability of oil droplets in liquid cleanser. There is no teaching or suggestion of using, in specific combination, fatty acid and the starch polymers of the invention.

Another type of well-known suspension agents used to stabilize oil droplets in liquid cleansers are high molecular weight, water-soluble polymers such as polyacrylate, modified celluloses and guar polymers as disclosed broadly, for example, in U.S. Pat. No. 5,661,189 to Grieveson et al. and U.S. Pat. No. 5,854,293 to R. W. Glenn, Jr. (assigned to Procter & Gamble). These polymeric stabilizers are also specifically described, for examples, in U.S. Pat. No. 5,905,062 to Elliott et al. (P&G) claiming hydrophobically modified nonionic cellulose for liquid stability, in U.S. Patent No. 6,172,019 B1 to Dehan et al. (Colgate-Palmolive) using combination of two separate polyacrylic acid polymers and in U.S. Pat. No. 6,001,344 to Villa et al. (Unilever) using the combination of xanthan gum and Carbopol® as a novel structuring system for stable liquid cleansing composition.

Although these polymeric materials are useful for suspending oil droplets in personal liquid cleanser, their thickening/structuring property depends on the liquid cleanser composition, i.e. surfactant type, surfactant level, emollient oil and other additives. As shown in the comparative examples of this invention, these water-soluble polymers tend to separate from the surfactant solution and lose their thickening/structuring property at elevated temperature storage conditions due to incompatibility of these polymeric thickeners with surfactants. To stabilize the liquid cleanser, high level of polymer is required which can in turn cause difficulty in processing and can impart an undesirable lumpy appearance and slimy feel during the use of the product.

Without imparting negative effects on important cleanser properties (such as appearance, lather, in-use/after-use sensory properties and its processability), applicants have found that storage stable liquid cleansers containing emollient oils and/or particles, (e.g., 1 to 30% by wt.) can be formulated using structuring system comprising specific water soluble/or swellable starch polymers combined with linear $C_8$ to $C_{13}$ fatty acids. Using the polymer/fatty acid structuring system as described in this invention, personal liquid cleansers with non stringy, non lumpy appearance, lotion-like rheology, excellent lather and storage stability can be easily formulated.

Liquid cleansers containing fatty acids are widely described in the art such as in WO 94/17166 to Giret et al, WO 94/18737 to Cothran et al. (P&G), U.S. Pat. No. 5,132,037 to Green et al., U.S. Pat. No. 5,234,619 to Green et al. and U.S. Pat. No. 5,290,470 to Green et al. (Unilever). These patents disclose the use of crystallized fatty acids either as skin benefit agents or as structuring agents. U.S. Pat. No. 5,360,580 to Rizvi et al teach the use of a long chain saturated fatty acid with polyethyleneamine to increase liquid stability. Liquid fatty acids such as oleic acid have been used as structurants to form lamellar structure with specific surfactant composition as described in U.S. Pat. Nos. 5,952,286 and 6,077,816 to Puvvada et al. (Unilever).

Again, none of these prior art references disclose the use of fatty acids of the invention combined with specific water soluble/or swellable starches as efficient structuring system for personal liquid cleansers. Furthermore, as shown in the examples of this invention, some of the fatty acid structured liquid cleanser compositions taught in these prior art references are not stable at elevated temperature especially when the total surfactant level is lower than 20 wt. %, more preferably lower than 15%.

By combining fatty acid and starch polymers, applicants have created a structuring system which provides stable emollient and/or particle containing compositions while at the same time maintaining good consumer desirable properties such as foaming, non-stringiness or non-lumpiness and soft smooth after wash moisturizing skin feel. In a preferred embodiment, this is done at relatively low (equal to or less than 25%, preferably equal to or less than 20%) surfactant levels.

BRIEF DESCRIPTION OF THE INVENTION

Specifically, the application relates to stable, personal product (e.g., personal wash or hair) liquid cleansing compositions comprising (by wt.):

(1) 2 to 30%, preferably 3 to 25%, more preferably 5 to 20% by wt. of a surfactant selected form the group consisting of anionic surfactants, nonionic surfactants, amphoteric surfactants, cationic surfactants or mixtures thereof;

(2) 0 to 30% (e.g., optional) preferably 1.0 to 25% skin benefit agent (e.g., emollient oil or benefit agent particle); and (3) a structuring system comprising:
  (i) linear fatty acid or acids of carbon chain length about 8 to 13; and
  (ii) 0.5 to 15%, preferably 0.5 to 10% total composition modified or non-modified starch, wherein the ratio of fatty acid or acids to said surfactants is from 1.0/9.0 to 3.5/6.5, preferably 1.5/8.5 to 3.0/7.0;

wherein said surfactants and the linear fatty acid or acids form a cloudy solution at 15% total wt. surfactant and fatty acids when measured at pH in the range of 4.5 to 7.0 and the amount of fatty acid/surfactant particles (and of fatty acid-surfactant complex) formed in the said liquid composition is more than 20 wt. %, preferably more than 30 wt. % based on the total weight of surfactants and fatty acids;

wherein the pH of said composition is 4.5 to 7.5, preferably 5.0 to 7.0; and wherein said composition is stable at both room temperature and 45° C. for over 3 weeks with no visible phase separation.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in Si units unless specified otherwise. All documents cited are—in relevant part—incorporated herein by reference.

DETAILED DESCRIPTION OF THE INVENTION

The present invention relates to personal products (e.g., personal wash) liquid cleanser compositions which both comprise an emollient oil and/or particles and are very stable. Moreover, stability is not provided at the expense of lumpy looking and/or slimy-feeling compositions. Specifically, the combination of specific starches and fatty acid in defined ranges (i.e., ratio of fatty acid to surfactants) provides a structuring system yielding stability while avoiding product negatives.

Specifically, the application relates to stable, personal product (e.g., personal wash or hair) liquid cleansing compositions comprising (by wt.):

(1) 2 to 30%, preferably 3 to 25%, more preferably 5 to 20% by wt. of a surfactant selected form the group consisting of anionic surfactants, nonionic surfactants, amphoteric surfactants, cationic surfactants or mixtures thereof;

(2) 0 to 30%, preferably 1.0 to 25% skin benefit agent (e.g., emollient oil or benefit agent particle); and (3) a structuring system comprising:
  (i) linear fatty acid or acids of carbon chain length about 8 to 13; and
  (ii) 0.5 to 15% preferably 0.5 to 10% total composition modified or non-modified starch.

wherein the ratio of fatty acid or acids to said surfactants is from 1.0/9.0 to 3.5/6.5, preferably 1.5/8.5 to 3.0/7.0;

wherein said surfactants and the linear fatty acid or acids form a cloudy solution at 15% total wt. surfactant and fatty acids when measured at pH in the range of 4.5 to 7.0 and the amount of fatty acid/surfactant particles (and of fatty acid-surfactant complex) formed in the said liquid composition is more than 20 wt. %, preferably more than 30 wt. % based on the total weight of surfactants and fatty acids;

wherein the pH of said composition is 4.5 to 7.5, preferably 5.0 to 7.0; and wherein said composition is stable at both room temperature and 45° C. for over 3 weeks with no visible phase separation.

The composition is defined in greater detail below:

Surfactant System

Anionic Surfactants

The anionic surfactant may be, for example, an aliphatic sulfonate, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or an aromatic sulfonate such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 0.5, preferably between 1 and 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, alkyl glycinate, alkyl glutamate, $C_8$–$C_{22}$ alkyl phosphates, alkyl phosphate esters and alkoxyl alkyl phosphate esters, acyl lactates, $C_8$–$C_{22}$ monoalkyl succinates and maleates, sulphoacetates, and acyl isethionates.

Sulfosuccinates may be monoalkyl sulfosuccinates having the formula:

$$R^4O_2CCH_2CH(SO_3M)CO_2M;$$

amido-MEA sulfosuccinates of the formula $$R^4CONHCH_2CH_2O_2CCH_2CH(SO_3M)CO_2M$$

wherein $R^4$ ranges from $C_8$–$C_{22}$ alkyl and M is a solubilizing cation;
amido-MIPA sulfosuccinates of formula $$RCONH(CH_2)CH(CH_3)(SO_3M)CO_2M$$

where M is as defined above.

Also included are the alkoxylated citrate sulfosuccinates; and alkoxylated sulfosuccinates such as the following:

$$R-O-(CH_2CH_2O)_n\overset{O}{\overset{\|}{C}}CH_2CH(SO_3M)CO_2M$$

wherein n=1 to 20; and M is as defined above.

Sarcosinates are generally indicated by the formula $RCON(CH_3)CH_2CO_2M$, wherein R ranges from $C_8$ to $C_{20}$ alkyl and M is a solubilizing cation.

Taurates are generally identified by formula $R^2CONR^3CH_2CH_2SO_3M$ wherein $R^2$ ranges from $C_8$–$C_{20}$ alkyl, $R^3$ ranges from $C_1$–$C_4$ alkyl and M is a solubilizing cation.

Another class of anionics are carboxylates such as follows:

$$R-(CH_2CH_2O)_nCO_2M$$

wherein R is $C_8$ to $C_{20}$ alkyl; n is 0 to 20; and M is as defined above.

Another carboxylate which can be used is amido alkyl polypeptide carboxylates such as, for example, Monteine LCQ® by Seppic.

Another surfactant which may be used are the $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 0.5–15% by weight of the total composition. Preferably, this component is present from about 1 to about 10%.

The acyl isethionate may be an alkoxylated isethionate such as is described in Hardi et al., U.S. Pat. No. 5,393,466, hereby incorporated by reference into the subject application.

In general the anionic component will comprise from about 1 to 25% by weight of the composition, preferably 2 to 15% by weight of the composition.

Zwitterionic and Amphoteric Surfactants

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

$$R^2-Y^{(+)}\underset{|}{\overset{(R^3)_x}{}}-CH_2-R^4Z^{(-)}$$

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:

4-[N,N-di(2-hydroxyethyl)-N-octadecylammonio]-butane-1-carboxylalte;
5-[S-3-hydroxypropyl-S-hexadecylsulfonio]-3-hydroxypentane-1-sulfate;
3-[P,P-diethyl-P-3,6,9-trioxatetradexocylphosphonio]-2-hydroxypropane-1-phosphate;
3-[N,N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl)ammonio]-butane-1-carboxylate;
3-[S-ethyl-S-(3-dodecoxy-2-hydroxypropyl)sulfonio]-propane-1-phosphate;
3-[P,P-dimethyl-P-dodecylphosphonio]-propane-1-phosphonate; and
5-[N,N-di(3-hydroxypropyl)-N-hexadecylammonio]-2-hydroxy-pentane-1-sulfate.

Amphoteric detergents which may be used in this invention include at least one acid group. This may be a carboxylic or a sulphonic acid group. They include quatemary nitrogen and therefore are quaternary amido acids. They should generally include an alkyl or alkenyl group of 7 to 18 carbon atoms. They will usually comply with an overall structural formula:

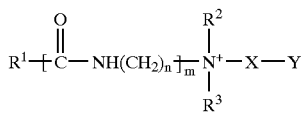

where $R^1$ is alkyl or alkenyl of 7 to 18 carbon atoms;
$R^2$ and $R^3$ are each independently alkyl, hydroxyalkyl or carboxyalkyl of 1 to 3 carbon atoms;
n is 2 to 4;
m is 0 to 1;
X is alkylene of 1 to 3 carbon atoms optionally substituted with hydroxyl, and
Y is —$CO_2$— or —$SO_3$—

Suitable amphoteric detergents within the above general formula include simple betaines of formula:

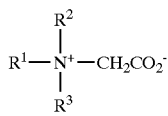

and amido betaines of formula:

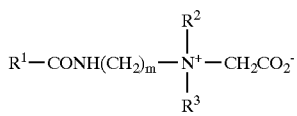

where m is 2 or 3.

In both formulae $R^1$, $R^2$ and $R^3$ are as defined previously. $R^1$ may in particular be mixture of $C_{12}$ and $C_{14}$ alkyl groups derived from coconut so that at least half, referably at least three quarters of the groups $R^1$ have 10 to 14 carbon atoms. $R^2$ and $R^3$ are preferably methyl.

A further possibility is that the amphoteric detergent is a sulphobetaine of formula

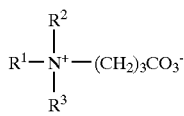

or

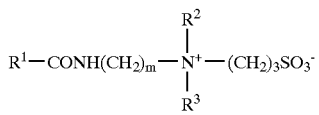

where m is 2 or 3, or variants of these in which —$(CH_2)_3SO^-_3$ is replaced by

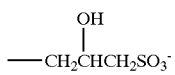

In these formulae $R^1$, $R^2$ and $R^3$ are as discussed previously.

Amphoacetates and diamphoacetates are also intended to be covered in possible zwitterionic and/or amphoteric compounds which may be used.

The amphoteric/zwitterionic surfactant, when used, generally comprises 0% to 15%, preferably 1 to 10% by weight of the composition.

In addition to one or more anionic and optional amphoteric and/or zwifterionic, the surfactant system may optionally comprise a nonionic surfactant.

Nonionic Surfactants

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$–$C_{22}$) phenols-ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference.

Preferred alkyl polysaccharides are alkylpolyglycosides of the formula

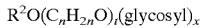

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

The total surfactants in the liquid cleanser composition can be in the range of 2 to 30 wt. %, preferably 3 to 25%, most preferably 5 to 20 %. For good lather, the combination of anionic surfactants and amphoteric/zwitterionic surfactants is preferred more than 40 wt % of the total surfactants, most preferably more than 60 wt. % of the total surfactant in the liquid cleanser composition of this invention.

Skin Benefit Agent

The skin benefit agents are defined as cosmetic grade organic, inorganic or polymeric materials that are not soluble (i.e., less than 1% soluble in the liquid composition) in the liquid cleanser composition. Examples of the benefit agent may comprise various classes of oils are as set forth below:

Vegetable oils: Arachis oil, castor oil, cocoa butter, coconut oil, com oil, cotton seed oil, olive oil, palm kernel oil, rapeseed oil, safflower seed oil, sesame seed oil and soybean oil, and avocado oil.

Esters: Butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate.

Animal Fats: Acetylated lanolin alcohols, lanolin, lard, mink oil and tallow.

Fatty acids and alcohols: Behenic acid, palmitic acid, stearic acid, behenyl alcohol, cetyl alcohol, eicosanyl alcohol and isocetyl alcohol; and insoluble salt of fatty acids such as calcium stearate or zinc stearate.

Other examples of oil/emollients include petrolatum, mineral oil, natural or synthetic wax, aloe vera, and polymeric benefit agent such as dimethyl polysiloxane, silicone elastomer, hydrogenated or non-hydrogenated polymers of alkylene or isoalkylene like polybutenes, polyalphaolefines, polyesters or polyacrylates, and mixture of above.

The agent may also include inorganic particles such as modified or non modified mica, Talc or TiO2. The benefit agent (e.g., emollient/oil) is generally used in an amount from about 0.1 to 30%, preferably 1 to 25% by wt. of the composition.

Particle size of the benefit agent can be in the range of 0.01 up to 500 micrometers, preferable 0.1 to 200 micrometers.

Structuring System

A key component of the liquid personal cleanser composition of the invention is the thickening/stabilizing system. The thickening/stabilizing system of this invention is a combination of fatty acids and modified or non-modified starch. Due to the synergistic effect between fatty acids and starches, liquid cleanser can be thickened and stabilized more effectively using the combination of fatty acid and starch than using either starch or fatty acid alone. More importantly, this novel thickening/stabilizing system works for a wide range of synthetic surfactants and liquid cleansers and allows compositions to have a viscosity ranging from pourable to lotion-like which can be easily formulated simply by changing the amount of starch or fatty acid added into the system.

Other than thickening/stabilizing the personal liquid composition, the system also helps the lather properties of synthetic surfactants. For example, cleansers containing this novel thickening/stabilizing system produce creamier lather than a cleanser without the novel stabilizing system of this invention. Each ingredient of this thickening/stabilizing system is described in details as following.

Fatty Acids

Fatty acids that are particularly useful for the invention are linear fatty acids having a carbon chain length in the range of 8 to 13, preferably 10 to 12 (for example, Prifrac®0 2906 or Prifrac® 2920 from Uniqema). Branched fatty acids, unsaturated fatty acids or longer chain length fatty acids ($C_{14}$ or higher) are not preferred, although they can be used, due to their antfoaming properties, especially when the synthetic surfactant level in the liquid composition is less than 15%. (Thus a preferred embodiment of the structuring system comprises $C_8$ to $C_{13}$ linear fatty acids and less than 15% surfactant.) The preferred linear fatty acids work with water-dispersible or water-soluble starch to structure low surfactant liquid cleanser compositions and function as an efficient foam booster for mild synthetic surfactants. To work both as a structuring agent and as a foam booster, the preferred linear fatty acid or acids in the claimed liquid composition should be partially neutralized. The degree of neutralization should be in the range of 10 to 80 wt %, preferably 20 to 60 wt % of the fatty acid or acids. This can be controlled by the pH of the liquid cleanser composition which should be in the range of 4.5 to 7.5, preferably 5.0 to 7.0. While not wishing to be bound by theory, it is believed that the superior lather properties of the preferred liquid cleanser composition are due to better solubility of the neutralized linear $C_8$ to $C_{13}$ fatty acids in the surfactant solution when the liquid cleanser composition is being diluted with water during the use of the product.

The level of preferably linear fatty acids in the liquid cleanser composition depends on the amount of synthetic surfactants in the liquid composition. For good lather and excellent stability, the weight ratio of fatty acids to total synthetic surfactants should be in the range of 1.0/9.0 to 3.5/6.5, preferably from 1.5/8.5 to 3.0/7.0.

Furthermore, to work effectively together with starches to thicken and to stabilize the personal liquid cleanser, the fatty acids should form a turbid solution with the synthetic surfactants at a pH in the range of 4.5 to 7.5, preferably 5.0 to 7.0. This can be determined by making a surfactant/fatty acid mixture containing 12 wt. % of the desired synthetic surfactants and 3 wt. % of the desired preferably linear fatty acids at a pH of around 5.5 to 6.5, (pH is adjusted with KOH or citric acid solution). If the prepared surfactants/fatty acids solution is clear, then either the synthetic surfactant composition has to be changed or the level of fatty acids has to be increased until the solution becomes cloudy. The level of fatty acid in the liquid can be increased either by lowering the pH of the liquid or by increasing the ratio of fatty acid or acids to the synthetic surfactants. It is believed that the cloudiness is due to the formation of fatty acid-induced surfactant/fatty acid particles. Weight % of fatty acid-induced surfactant/fatty acid particles formed in the liquid can be determined by measuring the % solid of the liquid before and after separating the surfactant/fatty acid particles from the liquid. Separation of fatty acid/surfactant particles from the cloudy fatty acid/surfactant solution can be done by centrifugation. The amount of fatty acid-induced surfactant particles should be at least 15 wt. % of the total surfactant/fatty acids, preferable 25 wt. % or higher and no more than 85 wt. %. The stability of the liquid cleanser is believed to be achieved through the interaction of these surfactant/fatty acid particles with the starch particles through space filling. That is, a complex structure is believed to be formed between the surfactant/fatty acid particles and the starch particles which provides stability.

Starches

The starches of the invention are high molecular weight polysaccharides derived from plants such as corn, waxy corn, topioca, potato, wheat or rice. Plants synthesize starch and accumulate it in small discrete particles, called starch granules, having a size in the range of 1 to 100 micrometers depending on the source of plant. Nonmodified starch granules are insoluble in water at a temperature below 40° C. Starch can work as thickening or structuring agent only after the starch granules are dissolved or are highly swollen by water. This can be achieved either by heat or by chemical or physical modification of the starch granules.

For many starch granules (especially non-modified ones), heat is required to swell or to solubilize the starch particles. The temperature that is required to dissolve or to fully swell the starch granules varies with the plant source or the modification, if any, of a particular starch. For non modified starch granules, in general, potato starch gelatinizes at a lower temperature (around 65° C.) than waxy maize starch (around 70° C.) which, in turn, gelatinizes at a lower temperature than regular corn starch (around 75° C.). The gelatinization temperature (a critical temperature above which the intermolecular hydrogen bonds holding the granule together are weaker and the granule undergoes a rapid irreversible swelling by water) of a starch granule can be dramatically reduced by physically or chemically modifying the starch granule to make them suitable for low temperature processing.

For modified starch, broadly, there are two types of starch granules or powders. One is chemically modified with hydrophilic ionic or/and nonionic groups such as phosphate, sulfate, sulfonate, carboxylate, dialkyl/trialkyl amino or quaternary ammonium, hydroxylethyl or hydroxypropyl group. The chemically-modified starch granule has lower gelatinization temperature than the original starch granule. In general, the gelatinization temperature decreases with increasing level of substitution. At high degree of substitution, the chemically modified starch granule becomes swellable even in cold-water. The other type of starches is pregelatinized cold water soluble or swellable starch powders which disperse and dissolve easily in cold water without the need of heating. These cold water soluble starch powders have been gelatinized and dried to from starch powders, so it will disperse and swell in cold water. Both non-modified starch granules and chemically or physically modified starches are suitable as thickening/structuring agent combining with fatty acids described above for personal liquid cleansers application of this invention.

In the subject invention, swelling or dissolution of starch granules can be done either with or without the presence of surfactants at a temperature higher than the gelatinization temperature of the specific starch granule. Higher processing temperature, in general, produces liquid cleansers with higher viscosity or better suspension properties due to higher swelling or better solubilization of these starch granules. It is preferred to process the starch granules or powders in the presence of surfactants. In the presence of surfactants, these starch granules or powders swell to form starch gel particles after being processed at a temperature higher than its gelatinization temperature to thicken, structure and stabilize the liquid cleanser composition of this invention. Due to the way of the liquid cleanser is stabilized by the swollen starch gel particles, the liquid cleanser of this invention has very shear thinning rheology, non stringy, non lumpy smooth appearance, and easy to disperse in water during the use of the product.

In general, whatever starch is used, it is preferred that the starch granule, upon use in the final composition, swell at least 200% by volume, preferably at least 400%, more preferably at least 600%, and most preferably at least 800% by volume to form swollen starch gel particles with size in range 2 to 300 micrometers.

Examples of starch granules which require heat to swell or to dissolve in water to thicken water are National 1545, Amioca corn starch, Structure Soaln (a modified potato starch), Clearjel, Hi Flo, National 1333, Colflo 67, National Frige, Novation 1600, Novation 2700 or Purity 420. Examples of cold water swelling modified starch powders are Ultra-Sperse modified tapioca or waxy maize starch, Stir-N-set modified tapioca starch, National 5717 pregelatinized modified waxy maize starch, National 1215 pregelatinized unmodified corn starch or Structure ZEA, a hydroxypropyl modified corn starch. All the starches mentioned above are commercially available from National Starch and Chemical Company. Examples of other commercially available chemically modified starch granules are PureGel B990, PureGel B992, PureGel B980 or non-modified starches are PureDent starches from Grain Processing.

Depending on the processing temperature, the starch thickening efficiency, the amount and composition of surfactants used in the cleanser, the pH of the liquid, the additives in the liquid cleanser composition and the desired final liquid viscosity, the amount of modified and/or non-modified starch granules or starch powders in the liquid can be in the range 0.5 to 15 wt. %, preferably 1 to 10%, most preferably 1 to 6 wt. %. The final viscosity of the liquid should be in the range of 10 to 400 Pascal, preferably in the range of 20 to 300 Pascal, most preferably in the range of 40 to 200 Pascal at 1 $sec^{-1}$ when measured at 25° C. using Haake RV20 Rotovisco Rheometer with SV1ST spindle. If the viscosity is lower than 10 Pascal, the prepared composition is not stable at room temperature and the starch gel particle precipitates out of the composition to form separate gel phase at the bottom of the liquid. If it is higher than 400 Pascal, the liquid is too pasty to process and to disperse easily during the use of the product.

In addition, the compositions of the invention may include optional ingredients as follows:

Water-soluble skin benefit agent, an essential optional ingredient that is preferred to be included in the liquid composition. A variety of water-soluble skin benefit agents can be used and the level can be from 1 to 30 weight %, preferably 1 to 20% by wt. Skin conditioning effect of deposited oils can be enhanced by addition of these water-soluble skin benefit agents. The materials include, but are not limited to, polyhydroxy alcohols such as glycerol, propylene glycol, sorbitol, pantenol and sugar; urea, alpha-hydroxy acid and its salt such as glycolic or lactic acid; and low molecular weight polyethylene glycols with molecular weight less than 20,000. Preferred water soluble skin benefit agents for use in the liquid composition are glycerol, sorbitol and propylene glycol.

Cationic polymer, another highly desirable optional ingredient may be used in the composition to provide the preferred skin feel and to enhance the deposition of skin benefit agent with particle size less than 10 micrometers. Examples of cationic polymers are modified polysaccharides including cationic guar available from Rhone Poulenc under the trade name Jaguar C13S, Jaguar C14S, Jaguar C17, or Jaguar C16; cationic modified cellulose such as UCARE Polymer JR 30 or JR 40 from Amerchol; N-Hance 3000, N-Hance 3196, N-Hance GPX 215 or N-Hance GPX 196 from Hercules; synthetic cationic polymer such as MerQuat 100, MerQuat 280, Merquat 281 and Merquat 550 by Nalco; cationic starches, e.g., StaLok® 100, 200, 300 and 400 made by Staley Inc.; cationic galactomannans based on guar gum of Galactasol 800 series by Henkel, Inc.; Quadrosoft Um-200; and Polyquaternium-24.

Auxiliary thickeners, such as carboxymethylcellulose, xanthan gum, magnesium aluminum silicate, hydroxyethylcellulose, methylcellulose, carbopols, glucamides, or Antil® from Rhone Poulenc; perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy4,2'4' trichlorodiphenylether (DP300); preservatives such as dimethyloldimethylhydantoin (Glydant XL1000), parabens, sorbic acid etc.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) and Vitamin A, C & E or their derivatives may be used advantageously in amounts of about 0.01% or higher if appropriate.

Polyethylene glycols which may be used include:

| Polyox | WSR-205 | PEG 14 M, |
| Polyox | WSR-N-60K | PEG 45 M, or |
| Polyox | WSR-N-750 | PEG 7 M. |

Thickeners which may be used include Amerchol Polymer HM 1500 (Nonoxynyl Hydroethyl Cellulose); Glucam DOE 120 (PEG 120 Methyl Glucose Dioleate); Rewoderm® (PEG modified glyceryl cocoate, palmate or tallowate) from Rewo Chemicals; Antil® 141 (from Goldschmidt).

Another ingredient which may be included are exfoliants such as polyoxyethylene beads, walnut sheets and apricot seeds and solid inorganic particles such as Talc and silicate. Capsules like perfume capsules or oil capsules can also be used.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight.

EXAMPLES 1–9

Synergistic Effect Between Fatty Acid and Starch for Liquid Stability

In order to show the synergistic effect between starch and fatty acids to stabilize liquid, applicants set forth Examples 1–9 as noted in Table 1 below:

TABLE 1

| Example | 1 | 2 | 3 | 4 | 5 | 6 | 7 | 8 | 9 |
|---|---|---|---|---|---|---|---|---|---|
| Na laureth(2) sulfate | 6.4 | 9.6 | — | — | — | 8 | 8 | — | 8.0 |
| Na lauroamphoacetate | 3.2 | 4.8 | — | 1 | 2 | 4 | 4 | — | 4.0 |
| Na cocamyldipropyl betaine | — | — | — | — | — | — | — | 4 | — |
| Na laurylsulfosuccinate | — | — | 7 | 3 | 6 | — | — | — | — |
| Alkylpolyglycoxide (Plantanan 2000) | — | — | 5 | 2 | 4 | — | — | — | — |
| Ammonium laureth(0.5) sulfate | — | — | — | — | — | — | — | 7 | — |
| Cocamide MEA | — | — | — | — | — | — | — | 0.66 | — |
| PEG-5 cocamide | — | — | — | — | — | — | — | 0.34 | — |
| Capric acid | 1.2 | 1.8 | 2 | 1.5 | 3.0 | 1.5 | 1.5 | 1.5 | 1.5 |
| Lauric acid | 1.2 | 1.8 | 1 | 0.5 | — | 1.5 | 1.5 | 1.5 | 1.5 |
| Starch (National 1545, ex. National Starch & Chemical) (unmodified corn starch) | 3 | 1 | 4 | 4 | 4 | 6 | 3.0 | 5 | — |
| Structure XL (pregelatinized chemically modified starch, ex. National Starch & Chemical) | — | — | — | — | — | — | — | — | 5.0 |
| Jaguar C13S | 0 | 0 | 0.2 | 0.1 | 0.1 | 0.35 | — | 0.2 | — |
| Glycerin | 5.0 | 5.0 | 5.0 | 3.0 | 5.0 | 5.0 | 25.0 | 3.0 | 5.0 |
| Petrolatum | 9.0 | 12.0 | 9.0 | 6.0 | 9.0 | — | 6.0 | 6.0 | 9.0 |
| Polybutene H1500 (polybutene ex. Amoco) | — | — | — | 2 | — | — | — | — | — |
| Sunflower seed oil | — | — | — | — | — | 12.0 | — | — | — |
| Perfume | 1.0 | 1.0 | 1.0 | 1.0 | 1.0 | 1.0 | 1.0 | 1.0 | 0.2 |
| Glydant plus | 0.2 | 0.2 | 0.2 | 0.2 | 0.2 | 0.2 | 0.2 | 0.2 | 0.2 |
| Deionized water | To 100 | To 100 | To 100 | To 100 | To 100 | To 100 | To 100 | To 100 | To 100 |

All measured in % by wt.

The pH of liquid was adjusted to 6.7 to 6.9 using either 30% citric acid or 40% KOH solution.

This novel fatty acid/starch thickening/stabilizing system is very robust and works for a wide range of surfactant compositions, surfactant levels and various types of benefit agents (e.g. emollient oils). All the liquids shown in these examples have good lather, nice appearance, and excellent storage stability. Examples 1 to 8 were prepared by first mixing deionized water, surfactants and fatty acid at 75 to 80° C. to form a uniform mixture. Starch granule (National 1545, modified waxy maze for examples 1 to 8) was then added into the surfactant/fatty acid mixture as 30% dispersion in deionized water and mixed for 5 minutes at 75 to 80° C. (order of addition is not critical). A calculated amount of KOH solution was added to adjust the pH to the range of 6.7 to 6.9. The starch was swollen/or dissolved in the surfactant solution by continuing mixing at 75 to 80° C. for 20 to 30 minutes, and the solution was cooled. Jaguar C13S, if used, was pre-dispersed in glycerin and added into the surfactant/fatty acid/starch mixture during cooling. Perfume, glydant plus and other ingredient were added at a temperature below 35° C. The emollient oil was mixed with the liquid at a temperature below 35° C. Final pH was checked and adjusted either with KOH or citric acid solution to around 6.8. Example 9 was prepared using a similar procedure described above except for the way of adding the starch power (Structure XL, pregelatinized starch). The starch powder was added together with the deionized water, surfactants and fatty acids before the mixture was heated and mixed at 75°–80° C. All the examples prepared were found to be stable at both 45° C. and room temperature for over one month.

COMPARATIVE EXAMPLES 1A TO 5B

In order to show that there is synergy only when both linear C8 to C13 fatty acids and starch are used, eight liquids with compositions same as Examples 1, 2, 3, 4, 5, 6 and 9 but containing only fatty acids or starch, but not both together, were prepared for comparison. Another liquid (Comparative example 2C) with composition same as Example 2 was also prepared using combination of myristic acid (linear fatty acid with carbon chain length of 14) and starch to show effect of fatty acid chain length on liquid stability. Preparation was as for example 1–9. Compositions of these comparative examples are shown in Table 2 below.

COMPARATIVE EXAMPLES 1A TO 5B

Liquids Containing Either Starch or Fatty Acids, not Both or $C_{14}$ Chain Length Fatty Acid chemically modified corn starch granule with gelatinization temperature around 55° C. Examples 10, 11, 12 and 14 were prepared using the same procedure described at Examples 1–9, except for the processing temperature, to swelVor dissolve the starch particles. That is, starch was added to mixture of surfactants, fatty acid and water rather than being premixed with water first. The processing temperature to swell/or dissolve the starch particles for each example 10–14 is shown in the Table 3 below. Example 13 was prepared by mixing starch granules with deionized water at 80 to 83° C. to form a pasty starch solution first. Surfactants, fatty acid and other ingredients were than added and mixed with the fully hydrated starch.

Examples 10 and 11 are pourable viscous liquids and the other three samples (examples 12, 13 and 14) all have lotion-like appearance. Samples prepared at higher starch swelling processing temperature had higher viscosity and better stability. For example, example 12, which was processed at 73° C., had much higher viscosity than example 10, which has the same composition as example 12 but was processed at a lower temperature. The viscosity of Example 12 is about 65 Pas. at 1 $S^{-1}$ vs. 20 to 25 Pas. for Examples 10. The viscosity was measured at room temperature using a Haaker R20 Viscometer. All the samples, except Example 10, were stable at both room temperature and 45° C. for over

TABLE 2

| Comparative Example | 1A | 2A | 2B | 2C | 3A | 4A | 5A | 5B |
|---|---|---|---|---|---|---|---|---|
| Na laureth(2) sulfate | 6.4 | 9.6 | 9.6 | 9.6 | — | — | — | — |
| Na lauroamphoacetate | 3.2 | 4.8 | 4.8 | 4.8 | — | 1 | 2 | 2 |
| Na laurylsulfosuccinate | — | — | — | — | 7 | 3 | 6 | 6 |
| APG (Alkylpolyglycoxide) (Plantanan 2000) | — | — | — | — | 5 | 2 | 4 | 4 |
| Capric acid | 1.2 | 1.8 | — | — | 2 | 1.5 | 2 | — |
| Lauric acid | 1.2 | 1.8 | — | — | 1 | 0.5 | 1 | — |
| Myristic acid ($C_{14}$) | — | — | — | 3.6 | — | — | — | — |
| Starch(National 1545, ex. National Starch & Chemical) | 0 | 0 | 3.0 | 3.0 | 0 | 0 | 0 | 4 |
| Structure XL (ex. National Starch & Chemical) | — | — | — | — | — | — | — | — |
| Jaguar C13S | 0 | 0 | 0 | 0 | 0.2 | 0.1 | 0.1 | 0.1 |
| Glycerin | 5.0 | 5.0 | 5.0 | 5.0 | 5.0 | 3 | 5.0 | 5.0 |
| Petrolatum | 9.0 | 12 | 12 | 12 | 9.0 | 6.0 | 9.0 | 9.0 |
| Polybutene | — | — | — | — | — | 2 | — | — |
| Perfume | 1.0 | 1.0 | 1.0 | 1.0 | 1.0 | 1.0 | 1.0 | 1.0 |
| Glydant plus | 0.2 | 0.2 | 0.2 | 0.2 | 0.2 | 0.2 | 0.2 | 0.2 |
| Deionized water | To 100 | To 100 | To 100 | To 100 | To 100 | To 100 | To 100 | To 100 |

The pH of liquid was adjusted to 6.7 to 6.9 using either 30% citric acid or 40% KOH solution. All measured in percent by wt.

All these samples were not stable at high temperature or room temperature storage condition. They all showed phase separation in less than 14 days at 45° C.

EXAMPLES 10–16

Examples 10 to 16 show the effect of process temperature and type of starch on the liquid properties of this invention. Example 10 is prepared for comparison. National 1545 starch is modified waxy maze starch granule which is not soluble or swellable at a temperature below 50° C. UltraSperse A is cold water soluble derived from waxy maze starch. Both starches are available from National Starch & Chemical Company. PureGel B990 from Grain Processing is 1 month. Example 10, (Comparative) showed phase separation after 4 weeks in 45° C. These examples show that the degree of swelling of starch particles in the personal liquid cleanser composition is a key component to the physical stability of the liquid. The degree of swelling of starch particles in the liquid composition, in turn depends on the processing temperature and modification of the starch granules. Thus Example 10, for example (with starch which is not water soluble starch and processed at 42–45° C.) provides slightly less stability than Example 13 (where water soluble starch is used) It is preferred that degree of swelling of starch granules in the liquid composition was at least 200% by volume, most preferably 600% by volume. With good degree of swelling, less starch (example 13 vs. example 10) or lower processing temperature (example 14 vs. example 10) can be used to make personal cleansing liquids with higher viscosity and better storage stability.

TABLE 3

| Examples | 10 Comparative Example | 11 | 12 | 13 | 14 | 15 | 16 |
|---|---|---|---|---|---|---|---|
| Na laureth(2) sulfate | 8 | 8 | 8 | 8 | 8 | 8 | — |
| Na lauroamphoacetate | 4 | 4 | 4 | 4 | 4 | 4 | 5.7 |
| K Cocoyl glycinate | — | — | — | — | — | — | 10.3 |
| Capric acid | 1.5 | 1.5 | 1.5 | 1.5 | 1.5 | 1.5 | — |
| Lauric acid | 1.5 | 1.5 | 1.5 | 1.5 | 1.5 | 1.5 | 1.9 |
| Starch (National 1545*) | 5 | 5 | 5 | 3.0 | — | — | — |
| Cold water soluble starch (Ultra-Sperse A*) | — | — | — | — | 5.0 | — | — |
| PureGel B990 (Grain Processing) | — | — | — | — | — | 4.0 | 12 |
| Jaguar C13S | 0.3 | 0.3 | 0.3 | 0.3 | — | 0.1 | 0.05 |
| Glycerin | 5.0 | 5.0 | 5.0 | 5.0 | 5.0 | 5.0 | 6.0 |
| Petrolatum | 12.0 | 12.0 | 12.0 | 12.0 | 12.0 | 6.0 | 8.0 |
| Perfume | 1.0 | 1.0 | 1.0 | 1.0 | 1.0 | 1.0 | 0.25 |
| Glydant plus | 0.2 | 0.2 | 0.2 | 0.2 | 0.2 | 0.2 | 0.2 |
| Deionized water | To 100 | To 100 | To 100 | To 100 | To 100 | To 100 | To 100 |
| Process temperature to swell or/dissolve starch particles | 42–45° C. | 60–63° C. | 70–73° C. | 80–83° C. premix | 42–45° C. | 70–73° C. | 70–73° C. |
| Viscosity | 20–25 Pas | | | 60–65 Pas | | | |

All percent by wt.

The pH of liquid was adjusted to 6.7 to 6.9 using either 30% citric acid or 40% KOH solution.

COMPARATIVE EXAMPLES 6A–13A

Liquid Structured with Polymeric Thickeners

These comparative examples show the storage stability of personal liquid cleansers containing only polymeric thickener (rather than fatty acid/starch thickening system of the invention) as the stabilizer of the liquid. Various polymeric thickeners as taught in the art were evaluated. All examples except comparative example 8A were not stable at the storage condition of 45° C. for 1 month. All showed phase separation in less than 2 weeks. Although liquid cleanser stability can be enhanced by increasing the level of polymeric thickener, such as note in comparative example 8A, the resulting liquid is very thick, pasty and difficult to pour out of the bottle (e.g. beyond the range of 10 to 400 Pascal discussed above in text). During use, the liquid tends to lump on the skin and difficult to spread evenly during use. Furthermore, these comparative examples clearly demonstrate that excellent thickening/stabilizing properties when using a combination of starch and linear fatty acids of this invention.

TABLE 4

| Comparative Examples | 6A | 7A | 8A* | 9A | 10A | 11A | 12A | 13A |
|---|---|---|---|---|---|---|---|---|
| Na laureth(2) sulfate | 8.0 | 8.0 | 8.0 | 8.0 | 8.0 | 8.0 | 8.0 | 8.0 |
| Na lauroamphoacetate | 4.0 | — | 4.0 | 4.0 | 4.0 | 4.0 | 4.0 | 4.0 |
| Na cocamyldopropyl betaine | — | 4.0 | — | — | — | — | — | — |
| Carbopol (ETD2020) | 0.5 | 0.5 | 1.0 | | | | | |
| Hydrophobically modified Carbopol (Pemulene TR1) | — | — | — | 0.5 | — | — | — | — |
| Hydrophobically modified hydroxyethyl cellulose (Natrosol Plus) | — | — | — | — | 0.5 | — | — | — |
| Hydroxyethylcellulose (Natrosol 250HR) | — | — | — | — | — | 0.5 | — | — |
| Starch (National 1545) | — | — | — | — | — | — | 2.5 | |
| Jaguar C13S | — | — | — | — | — | — | 0.3 | 0.5 |
| Glycerin | 5.0 | 5.0 | 5.0 | 5.0 | 5.0 | 5.0 | 5.0 | 5.0 |
| Petrolatum | 0 | 9.0 | 9.0 | 9.0 | 9.0 | 9.0 | 9.0 | 9.0 |
| Sunflower seed oil | 9.0 | — | — | — | — | — | — | — |
| Perfume | 1.0 | 1.0 | 1.0 | 1.0 | 1.0 | 1.0 | 1.0 | 1.0 |
| Glydant plus | 0.2 | 0.2 | 0.2 | 0.2 | 0.2 | 0.2 | 0.2 | 0.2 |
| Deionized water | To 100 | To 100 | To 100 | To 100 | To 100 | To 100 | To 100 | To 100 |

All in percent by wt.
*Phase stable, but extremely viscous

What is claimed is:

1. Personal product liquid cleansing compositions comprising (by wt.):
   (1) 2 to 30% of a surfactant selected form the group consisting of anionic surfactants, nonionic surfactants, amphoteric surfactants, cationic surfactants or mixtures thereof;
   (2) 0 to 30%, benefit agent; and
   (3) a structuring system comprising:
      (i) $C_8$–$C_{13}$ linear fatty acid or acids; and
      (ii) 0.5 to 15% total composition modified or non-modified starch;
   wherein the ratio of linear fatty acid or acids to said surfactants is from 1.0/9.0 to 3.5/6.5;
   wherein said surfactants and fatty acid or acids form a cloudy solution containing surfactant/fatty acid particles at 15% total wt. surfactant and fatty acids, measured at a pH in the range of 4.5 to 7.5, the amount of surfactant/fatty acid particles formed is at least 15 wt % based on the total surfactants and fatty acids;
   wherein the pH of said liquid cleanser composition is 5.0 to 7.5; and wherein said composition is stable at both room temperature and 45° C. for over 3 weeks with no visible phase separation;
   wherein modified starch refers to chemical or physical modification to enhance dissolution or swelling of starch in water.

2. A composition according to claim 1, comprising 3 to 20% by wt. surfactant.

3. A composition according to claim 1, comprising 5 to 20% by wt. surfactant.

4. A composition according to claim 1, comprising less then or equal to 15% by wt. surfactant.

5. A composition according to claim 1, wherein benefit agent is in 0.5 to 25% by wt. range.

6. A composition according to claim 1, wherein benefit agent is a cosmetic grade organic, inorganic or polymeric material not soluble in liquid cleanser.

7. A composition according to claim 4, wherein not soluble is defined as less than 1 wt. % solubility of the active in the liquid cleanser.

8. A composition according to claim 6, wherein said benefit agent is an emollient oil or surfactant insoluble inorganic particle.

9. A composition according to claim 8, wherein said particle is chosen from modified or non-modified mica, talc, titanium dioxide, or mixtures thereof.

10. A composition according to claim 1, wherein said fatty acid or acids are $C_8$ to $C_{13}$ linear fatty acids and mixtures thereof.

11. A composition according to claim 10, wherein fatty acid or acids are $C_{10}$ to $C_{12}$ fatty acid or acids.

12. A composition according to claim 1, wherein ratio of fatty acids to surfactant is from 1.5 to 8.5 to 3.0 to 7.0.

13. A composition according to claim 1, wherein pH is 5.5 to 7.0.

14. A composition according to claim 1, comprising 0.5 to 10% by wt. modified or non-modified starch.

15. A composition according to claim 1, wherein modified starch are chemically or physically modified with ionic and/or nonionic hydrophilic groups to obtain gelatinization temperature in the range of 30° to 75° C.

16. A composition according to claim 15, wherein said hydrophilic ionic or nonionic groups are selected from phosphate, sulfate, sulfonate, carboxylate, dialkyl/trialkyl amino or quaternary ammonium, hydroxypropyl, hydroxyethyl groups, and mixtures thereof.

17. A composition according to claim 1, wherein modified starch is cold water pregelatinized starch powder.

18. A composition according to claim 1, wherein the amount of surfactant/fatty acid particle is in the range of 25 to 85 wt. % of total surfactant and fatty acids.

19. A composition according to claim 1, wherein starch swells to at least 200% by volume in final composition.

20. A composition according to claim 1, wherein starch granules swell in the liquid composition to size of 3 to 200 micrometers.

21. A composition according to claim 1, wherein 10 to 80% by wt. of fatty acids are neutralized.

22. A composition according to claim 1, wherein the viscosity is in the range of about 10 to 400 Pascal at 1 $sec^{-1}$.

* * * * *